United States Patent [19]

Hardcastle et al.

[11] Patent Number: 4,820,270
[45] Date of Patent: Apr. 11, 1989

[54] BALLOON CATHETER AND PROCESS FOR THE MANUFACTURE THEREOF

[76] Inventors: David Hardcastle; John C. Higginson, 10 Brindley Road, Gorse Lane Industrial Estate, both of Clacton-on-Sea, Essex; John W. Kennedy, The Master's Lodge, Flemish Cottages, Dedham, Essex, all of England

[21] Appl. No.: 82,284

[22] Filed: Aug. 6, 1987

Related U.S. Application Data

[63] Continuation of Ser. No. 918,506, Oct. 14, 1986, abandoned, which is a continuation of Ser. No. 617,998, filed as PCT GB83/00251 on Oct. 7, 1983, published as WO84/01513 on Apr. 26, 1984, abandoned.

[30] Foreign Application Priority Data

Oct. 8, 1982 [GB] United Kingdom ................. 8228837

[51] Int. Cl.⁴ ............................................ A61M 29/00
[52] U.S. Cl. ...................................... 604/96; 264/167; 264/176.1; 264/177.1; 604/101
[58] Field of Search ..................................... 604/96–99, 604/101–102; 264/176.1, 177.1, 167

[56] References Cited

U.S. PATENT DOCUMENTS 3,050,066 8/1962 Koehn ................................... 604/96
3,982,544 9/1976 Dyck ..................................... 604/96

FOREIGN PATENT DOCUMENTS 2054385 2/1981 United Kingdom ................. 604/96

Primary Examiner—C. Fred Rosenbaum
Assistant Examiner—Gene B. Kartchner
Attorney, Agent, or Firm—Cushman, Darby & Cushman

[57] ABSTRACT

The present invention relates to catheters and like devices for passage into a body cavity.

In the invention the device has a stem portion comprising at least a first tube disposed within a second tube, the tubes being joined at one pair of ends by a flexible member covering the opening of the passage formed between the inner tube and the outer tube. The flexible member is arranged such that the tubes are movable relative to each other and by movement of the inner tube away from or towards the one end of the outer tube the flexible member respectively either can be drawn within the adjacent one end of the outer tube to be enclosed within the outer tube or pushed outside the adjacent one end of the outer tube to expose a balloon. The balloon can be inflated within the body cavity using a fluid under pressure supplied to the balloon from outside the body through said passage.

25 Claims, 5 Drawing Sheets

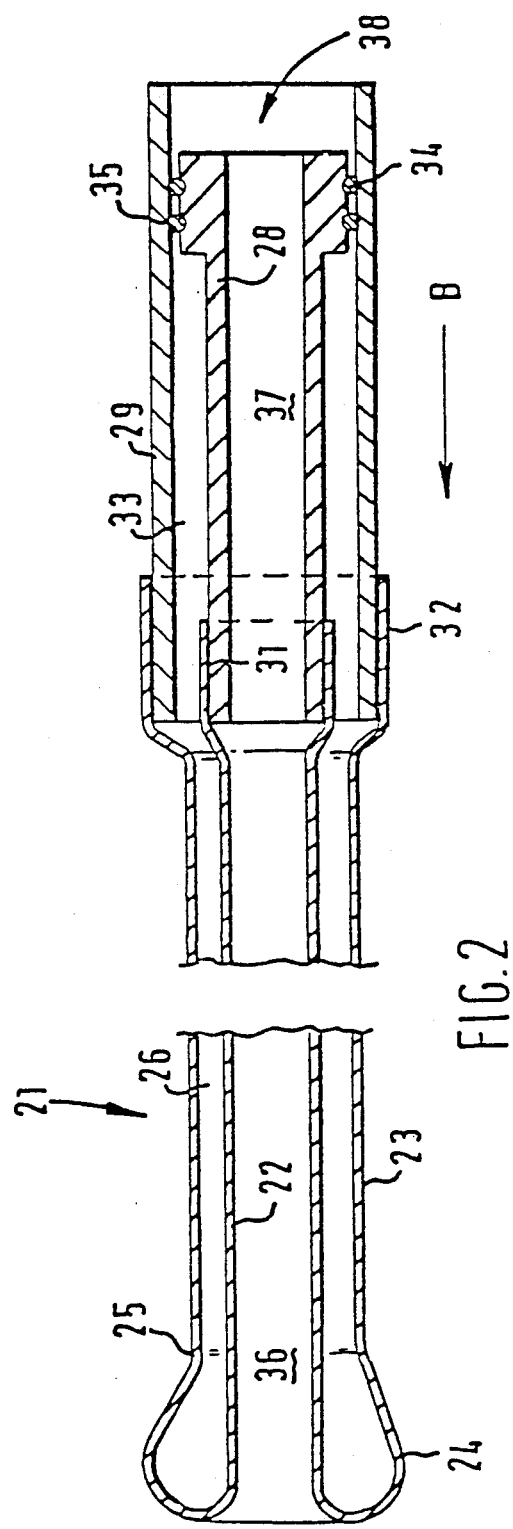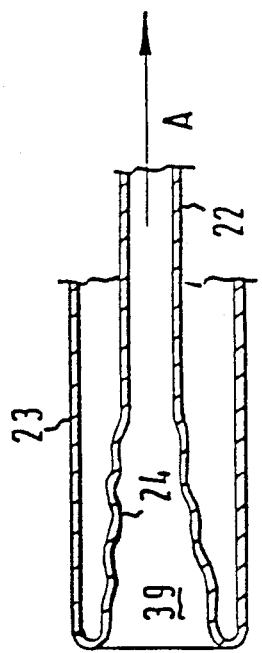
FIG.2
FIG.2(a)

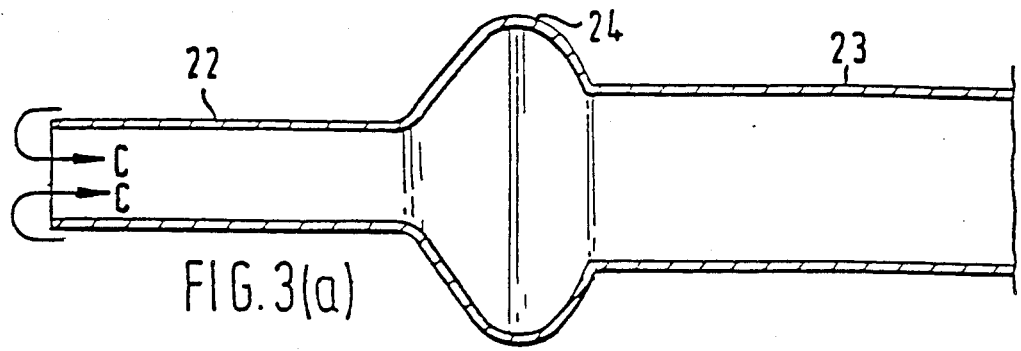
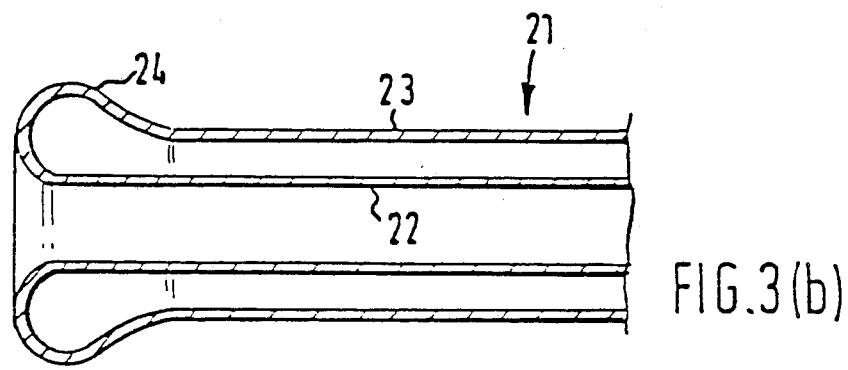
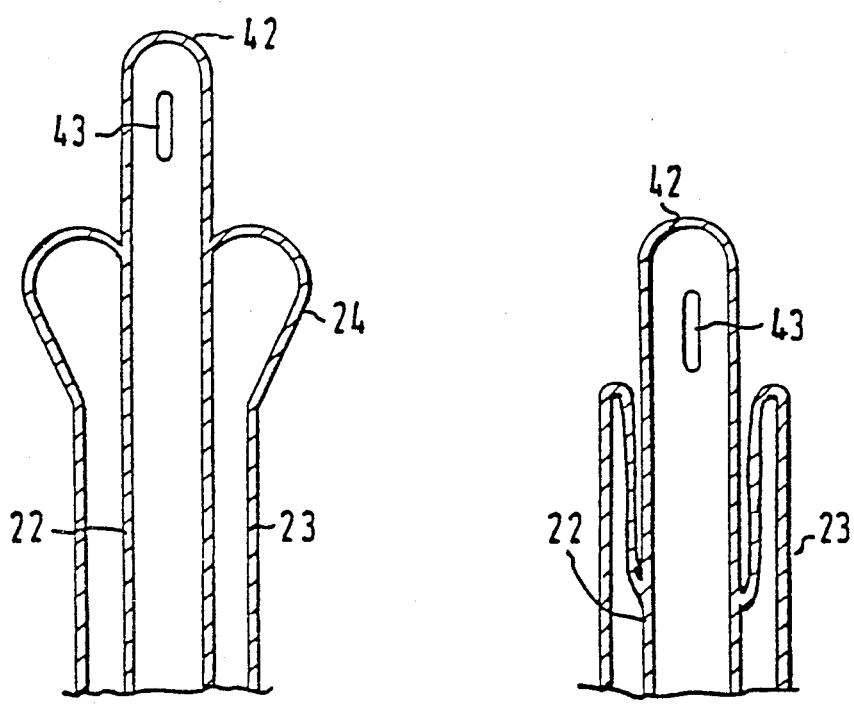

BALLOON CATHETER AND PROCESS FOR THE MANUFACTURE THEREOF

This is a continuation of application Ser. No. 918,506, filed Oct. 14, 1986, now abandoned, which is a continuation of Ser. No. 617,998, filed as PCT GB83/00251 on Oct. 7, 1983, published as WO84/01513 on Apr. 26, 1984, now abandoned.

The present invention relates to a device for passage into a body cavity, in particular to a novel construction of a catheter or the like.

From ancient times catheters have been used in medicine and surgery for draining fluids from a patient's body and for permitting access to the interior of a patient's body. They are most widely used today in the self-retaining form of the latex Foley catheter devised by Foley in the 1930's.

Since the 1930's catheters have been produced mainly from latex by dipping in a complicated process involving a relatively large number of process steps. In each of the known process steps there are opportunities for introducing defects into the final product which may render the product useless or at least inadequate for its intended medical purposes. Many of these defects will be detected during quality assurance inspection, giving high scrap rates for the product, which is a significant source of inefficiency that has to be reflected in the final cost of the catheter devices in the market place. However, worse still is the fact that a significant number of defective catheters escape detection during quality assurance inspection, reach the patient, and thus cause severe medical difficulties.

Since the 1940's research to improve catheter design has largely concentrated on improvements aimed at reducing local bodily reactions caused by the presence of foreign material within sensitive body areas. The result has been to improve design in terms of the employment of new polymeric materials, for example, siliconised latex, silicone elastomers, polyvinylchloride, polyurethane, "Teflon" coated latex, etc. Until now, however, there has been no major innovation in catheter design and construction which seeks to overcome the principal defect encountered with present catheter usage described below.

The principal source of most difficulties associated with previous designs of catheter lies in the requirement to provide an inflatable balloon affixed to the stem of the catheter which is intended to hold the catheter in position once inserted into the appropriate body cavity through a body orifice, e.g. into the bladder through the urethra in the case of a urinary catheter. The catheter at the same time must be constructed of a material stiff enough to allow it to be pushed into the body orifice and positioned within the associated body cavity, whereafter the balloon must be easily inflatable from outside the cavity, with inflation causing no partial or complete blockage of the inflation channel or lumen. In the event that complete blockage of the inflation channel or lumen occurs after inflation it becomes no longer possible to deflate the inflated balloon and withdrawal of the catheter is prevented. It is this problem of non-deflation of the catheter retaining balloon once inflated, particularly associated with catheters formed by a latex dipping operation, that is a principal defect of known catheters, as is well known to those familiar with this art.

When catheters contact living body tissues, there is a high likelihood of irritation occurring. Furthermore, body residues, such as clotted blood and lympth in the case of catheters placed in incisions, and bladder stones in the case of urinary tract catheters, tend to adhere to catheters, thus causing blockage of the drainage passage. Accordingly, frequent replacement of catheters is required in most use situations.

In attempting a catheter replacement it is important that deflection of the retaining balloon does in fact take place to the necessary degree. If the balloon fails to deflate when attempts are made to remove the inflation medium through the inflation channel or lumen, the patient is placed 'at risk' from the alternative procedures then made necessary to bring about deflation of the balloon prior to removal of the catheter. Such alternative procedures include:

(i) The injection of a chemical into the inside of the balloon so as to effect degradation of the balloon material. Frequently, ether is used to attack latex rubber and rupture a latex balloon. Ether, however, is highly irritant to the lining of body tracts (such as the urinary tract) and can thus give rise to subsequent medical conditions which require further treatment.

(ii) The application of a steel stillete, passed through the inflation channel or lumen of the catheter physically to rupture the balloon. This procedure carries with it the risk of perforating the wall of the body tract in which the catheter is located and may require subsequent surgical repair, thus again exposing the patient to 'risk'.

(iii) Inflation of the balloon to an excessive degree so that it is caused to rupture. In this procedure the balloon may disintegrate into fragments which, in the case of urinary catheters for example, can afford sources of phosphatic encrustations leading to eventual stone formation.

In addition, there is a so-called 'safe' procedure which involves rupturing the balloon by transversal insertion of a sterile intravenous gauge needle under radiological viewing conditions. This procedure, however, even when safe is complicated and expensive in equipment and time.

We have now found surprisingly that the production difficulties associated with previous catheter designs can be minimised and the risk of non-deflation of the retaining balloon essentially can be eliminated by providing a design which comprises two tubes of different diameter joined by a portion which can provide the necessary balloon when the tube of smaller diameter is disposed within the larger diameter tube.

Accordingly, the present invention provides a device for passage into a body cavity through a natural or surgical opening in the body, which device has a stem portion comprising at least a first tube disposed within a second tube, the tubes being joined at one pair of ends by a flexible member covering the opening of the passage formed between the inner tube and the outer tube, the flexible member being arranged such that the tubes are movable relative to each other and by movement of the inner tube away from or towards the one end of the outer tube the flexible member respectively either can be drawn within the adjacent one end of the outer tube to be enclosed within the outer tube or pushed outside the adjacent one end of the outer tube to expose a balloon which can be inflated within the body cavity using a fluid under pressure supplied to the balloon from outside the body through said passage.

The device of the invention generally will be a catheter, that is a device used to remove or supply a fluid to the body cavity with which it is associated. In such a catheter device the balloon generally should be simultaneously either inflated by advancing said inner tube towards said one end of the outer tube or deflated by retracting said inner tube away from said one end of the outer tube.

However, the device also may find application in removal of solid bodies from such cavities. Accordingly, while the description which follows is for convenience largely given in terms of a urinary catheter construction, it is to be understood the invention is intended to cover other related constructions and uses. In either or any event the device is preferably constructed from a radio-opaque thermoplastics material.

In the device of the invention the inner and outer tubes are preferably concentric tubes. In that case the balloon formed by the flexible member when exposed will essentially be an annular balloon.

The device according to the invention may include means remote from said balloon to permit the supply of a fluid under pressure to the passage formed between the inner and outer tubes. Preferably, such a device includes in communication with the said passage and providing said means a portion connectable to a syringe.

Alternatively, and more preferably, the device according to the invention includes means remote from said balloon to supply a fluid under pressure to the passage formed between the inner and outer tubes. In particular and preferred form the fluid supply means comprises a piston associated with the other end of the inner tube and disposed in fluid tight engagement within a cylinder associated with the other end of the outer tube. Also, such a piston/cylinder arrangement may, if desired, provide or be included within a suitable handle portion. In addition, if desired, the fluid supply means may be releasably connected to the two tubes.

The stem portion of the device of the invention may be manufactured in several ways using a combination of vacuumforming, blow-mould, and extrusion techniques. In one such process in-line extrusion may be employed and in another such process concentric tube extrusion may be employed. The invention, therefore, includes in one embodiment a process for forming a device in accordance with the invention, which process comprises the steps of:

(i) extruding a thermoplastics material through a die to form a required length of tube of a first diameter;

(ii) vacuum-forming or blow-moulding the end of the tube adjacent the die to form a balloon portion;

(iii) setting the die to a second diameter;

(iv) extruding the thermoplastics material through the die to form a required length of tube of said second diameter attached to the first diameter tube through the balloon portion; and (v) passing the smaller diameter tube into the larger diameter tube or the larger diameter tube over the smaller diameter tube to bring their remote ends adjacent each other.

The above process of our first embodiment requires in-line extrusion using an extruder fitted with a variable die for tube extrusion. In step (i) the die is set to extrude a first tube section to the tube length required. Then in step (ii) the working portion of tube is surrounded with a former or mould of appropriate shape to vacuum-form or blow-mould a suitable balloon portion. Next in step (iii) the die is reset to extrude a second tube section preferably of larger diameter to approximately the same tube length, after which the whole is cooled and the smaller diameter tube is inverted through the larger diameter tube or the larger diameter tube is passed over the smaller diameter tube. Finally, as necessary, the thus-formed stem may be affixed to a suitable handle constructed separately.

In another embodiment, the invention includes a process for forming a device in accordance with the invention, which process comprises the steps of:

(a) ejecting molten thermoplastics material from a die for extruding two concentric tubes;

(b) moulding e.g. blow-moulding or injection moulding, an annular balloon between the tube ends from the molten material; and (c) extruding the remainder of the concentric tubes to a required length.

The above process of our second embodiment requires an extruder fitted with a die for extruding two concentric tube sections. In step (a) a suitable amount of material is ejected from the die, to which in step (b) a blow- or injection-mould of appropriate shape is brought to cause formation of a balloon in the mould, for example, in the case of a blow-mould by injection of air between the concentric orifices of the extruder die. Then in step (c) extrustion of two concentric tubes is effected using the blow-mould or injection-mould as a clamp for haul-off, the tubes being extruded to the length required. Finally, the whole is cooled and any necessary handle is affixed thereto.

In a further embodiment, the invention includes a process for forming a device in accordance with the invention, which process comprises the steps of:

1. providing a required length of preformed tube of thermoplastics material having a first diameter;

2. disposing the tube in an essentially concentric relationship with a die for extruding a tube of thermoplastics material having a second diameter;

3. ejecting at least sufficient molten thermoplastics material from the die to form a balloon;

4. moulding e.g. blow-moulding or injection-moulding, an annular balloon between the end of the material in the die and the adjacent surface of the preformed tube; and 5. extruding a die-formed tube while passing the preformed tube in the same direction and at the rate of the extrusion.

Preferably, in the above further embodiment the preformed tube has a smaller diameter than the extruded tube. In addition, where a tipped catheter is required, a tip portion of the preformed smaller diameter tube should extend beyond the position at which the annular balloon is blow-moulded or injection-moulded.

Any manufacturing process of the kinds defined above must be carried out under clean conditions and the product, once finished, must be sterilised and suitably packaged to maintain sterility until the catheter is inserted. For example, in urethral catheters, meticulous asepsis is required to avoid potentially fatal ascending infection of the urethral tract.

The device of the invention may be manufactured from a variety of materials. In that respect, it will be appreciated by those familiar with techniques currently employed for manufacturing catheters that, because of the flexibility of choice permitted by the manner of construction of the present device, a much wider range of materials may be used in its manufacture. However, the material chosen in any particular context will be a material affording performance characteristics best suited to that context. In that respect, the main criteria to be kept in mind when selecting materials say for urinary catheters in particular are:

(a) the material must be stiff enough to allow the finished article to be passed through the urethra and into the bladder. However, stiffness may be reduced if the usual practice of lubricating the catheter is employed;

(b) for use in male patients the material must be flexible enough to allow the device to bend easily after passing the perineal membrane and again after entering the prostate gland;

(c) the material must remain flexible at body temperature so as to minimise discomfort to a catheterised patient resulting from movement;

(d) in the case of a tipped catheter of the kinds described below, the material forming the tip must be soft enough not to damage the urethral mucosa during insertion;

(e) the material must provide a balloon portion capable of being inflated. However, it should be noted in that respect that the inflation pressure with the present device is much less than that required in standard catheters.

Taking into account the above criteria, it may be desired to select a material from among known materials for the purpose, namely latex rubber, silicone elastomers, polyurethane elastomers, vinyl chloride polymers, and various siliconised polymers, i.e. polymer compositions including a proportion of a silicone material. Alternatively, other polymeric materials may be employed as desired.

Latex rubber has long been used for urinary catheters. It is the most commonly used material in the manufacture of such catheters today, but it has the disadvantage that it tends easily to form encrustations which can result in chemical urethritis. Accordingly, except in special circumstances it will not be a material of choice for the device of the present invention.

Silicone elastomers, i.e. silicone rubbers, offer considerable improvements over latex rubber and at present are used especially for long term catheterisation of up to several months or more. These materials are physiologically inert and much less prone to encrustation, although they have the disadvantage of being very much more expensive.

Polyvinyl chloride materials are suitable for medium-term catheterisation, probably up to about four months. While they are not as chemically inert as silicone elastomers, they may be used to produce devices having a thinner wall construction, and because of that the devices block less frequently. Devices formed of PVC tend to exhibit less encrustation and a low incidence of chemical urethritis than comparable devices formed of latex rubber, mainly due to the smooth surfaces provided by the fabrication techniques available for PVC. There is also evidence that the level of toxicity is lower with PVC than with latex rubber, and this in turn reduces the risk of urethral or bladder irritation and subsequent infection.

PVC materials tend to be firm at room temmperature and yet become more supple at body temperature. This makes the catheter devices constructed from PVC easy to insert and comfortable in use since they conform readily to the shape of the urethra. The main disadvantage is the stiffness of the material at the time of insertion if the device is inserted "cold", but this can be easily overcome by immersing the catheter device in sterile water at say 37° C. for two minutes prior to use. Alternatively, a more flexible grade of PVC may be chosen.

PVC materials also have the advantage that the use of a relatively rigid material allows suction to be applied while the catheter is in situ without the risk of collapsing the tube walls.

While the balloons of currently available PVC catheters are fabricated from latex, in the device of the present invention, where a PVC material is used, the same material will be used throughout at least the stem portion of the device, i.e. the two tubes and the interlinking flexible balloon.

In addition, various coating materials can be applied to most catheter materials with attendant upgrading of performance. For example PTFE (Teflon) coatings may be employed, thus affording a chemically-inert, smooth surface which considerably reduces the risk of encrustation. However, coated materials give rise to the disadvantage that there is a risk of delamination, which may leave particles of coating in the bladder, and those in turn may result in stone formation and other problems. Similarly, silicone elastomer coatings may be applied with advantages similar to those given by PTFE materials, but again with the attendant serious disadvantage of possible delamination.

Overall, it will generally be preferred to use polyvinyl chloride materials in the manufacture of devices in accordance with the invention. Alternatively, other preferred materials are poly (ether block amides) which may be obtained as thermoplastic elastomers combining the advantages of nylon and rubber. The poly (ether block amide) materials now commercially available are particularly useful in that they are free from plasticisers which can migrate. In addition, various silicones, in particular thermoplastic silicones may be employed.

The invention will now be described by way of example and mainly with reference to the accompanying drawings in which:

FIGS. 2 and 2(a) are diagrammatic representations of one form of catheter in accordance with the present invention;

Figure 4:
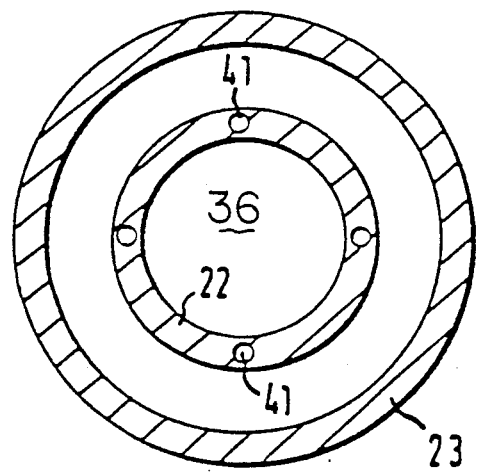
Figures 6A, 6B, 6C, 6D:
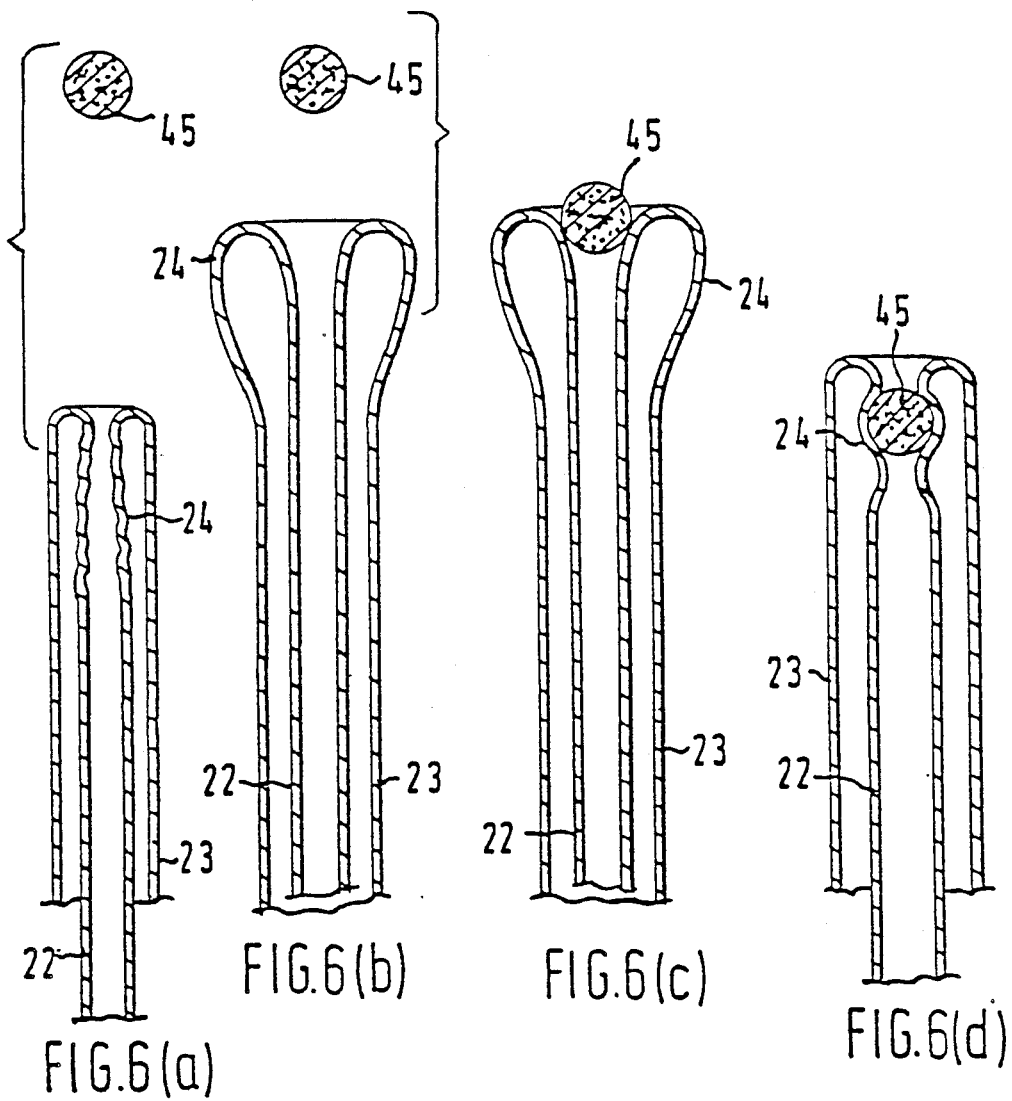

FIGS. 3(a) and 3(b) diagrammatically illustrate one process technique for forming the stem portion of the catheter of FIG. 2;

FIG. 4 is a cross-section through the stem of a catheter in accordance with the invention showing a variation to provide a "3-way" construction;

FIGS. 5(a) and 5(b) are diagrammatic representations of another form of catheter in accordance with the present invention; and FIGS. 6(a) and 6(d) show in diagrammatic form the use of a catheter stem as illustrated in FIG. 2 in the role of a foreign body removal instrument.

Figure 7:
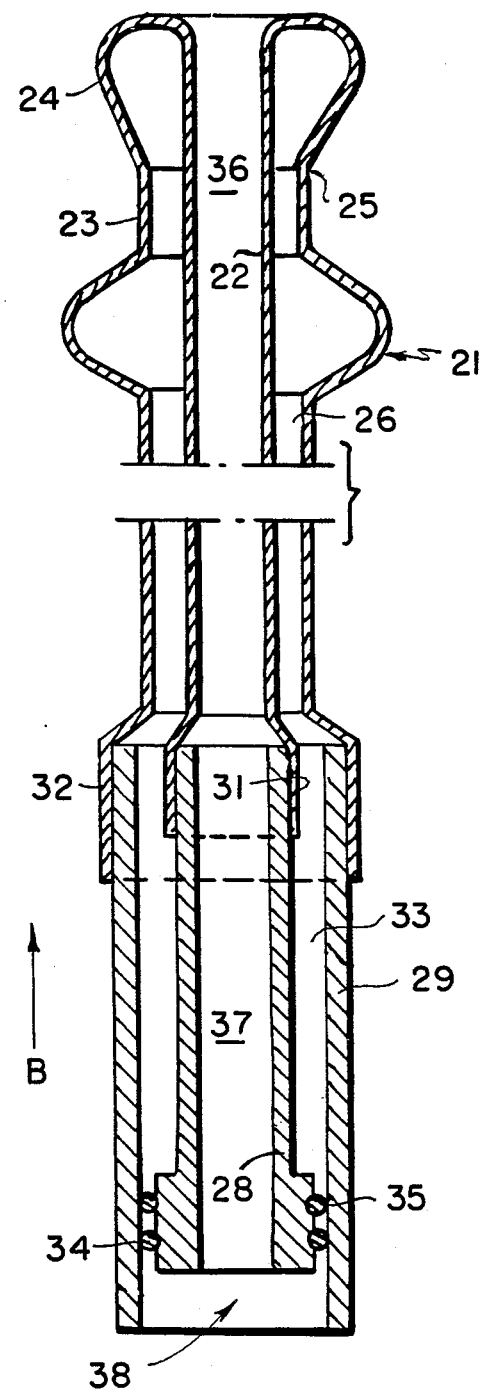

FIG. 7 is a diagrammatic representation of one form of the catheter of the present invention which includes a further flexible member formed in the outer tube whereby two balloons can be inflated in-line along the stem portion.

FIG. 7 is a diagrammatic representation of one form of the catheter of the present invention which includes a further flexible member formed in the outer tube whereby two balloons can be inflated in-line along the stem portion.

Figure 1:
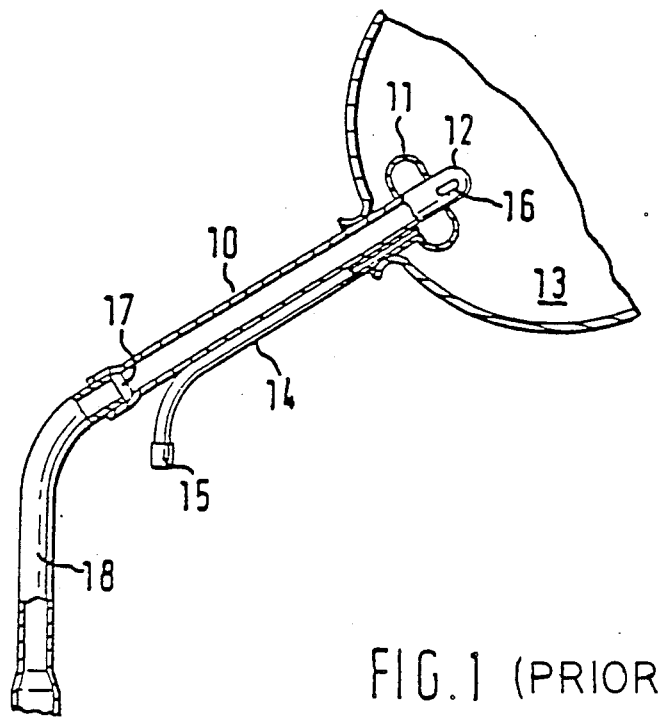
FIG. 1 is a diagrammatic representation of a Foley-type prior art catheter in situ.

Referring to FIG. 1, the prior art design of catheter shown comprises a drainage tube 10 having a balloon 11 at one end 12. The end 12 when positioned within say a bladder 13 may be retained there by inflating the balloon 11 via an inflation lumen 14 running along the tube 10, using a syringe attached to a connector 15. The end 12 of the tube 10 typically includes eyes 16 and the opposite end 17 of the tube 10 may be connected to additional tubing 18 to remove liquid and/or debris drained through the eyes 16 into the tube 10.

Referring to FIG. 2, the catheter of the invention shown comprises a stem portion 21 formed in one piece, and comprising an inner tube 22, an outer tube 23, and at one end thereof a balloon 24 covering and closing opening 25 of passage 26 formed between the two tubes. In the configuration shown in FIG. 2 the balloon 24 is at least partially inflated whereas in the configuration shown in FIG. 2(a) with the inner tube pulled back i.e. moved in the direction of arrow A, the balloon is deflated and pulled within the open end of the outer tube 23.

Attached to the opposite end of the stem portion 21 is a handle arrangement comprising a piston 28 disposed within a cylinder 29. The piston 28 is fixed to end 31 of tube 22 and the cylinder 29 is fixed to end 32 of tube 23, for example, by use of a suitable adhesive or by heat or solvent welding, so that fluid within chamber 33 and passage 26 cannot leak through the joints. (Alternatively, a moulded clip arrangement (not shown) may be employed). Similarly, a fluid seal between piston 28 and cylinder 29 is maintained by 'O' rings 34 and 35. Typically the passage 26 and chamber 33 may be filled with air or an inert liquid, preferably water.

As shown in FIG. 2 the inner tube 22, when the balloon 24 is at least partially inflated, provides an unrestricted drainage passage 36. That passage 36 is itself connected to a further passage 37 through the hollow body of piston 28, and other necessary or suitable tubing or connectors to enable fluid to be drained through the passages 36 and 37, may be provided at end 38 of the piston/cylinder arrangement.

In use the balloon is first retracted by any necessary movement in the direction of arrow A to the position shown in FIG. 2(a). The stem 21 is then inserted through a body orifice such as the urethra until end 39 of passage 36 is suitably disposed in the associated body cavity. Then the piston 28 is moved in the direction of arrow B to expose the balloon 24 and simultaneously at least partially to inflate the balloon. The balloon 24 then, as such or when more fully inflated by movement of piston 28 in direction B, acts to retain the catheter with its end 39 within the body cavity so that fluid etc. can drain off through passages 36 and 37. Preferably, the handle includes a locking device (not shown) to retain the piston in a position where the balloon remains inflated.

To deflate the balloon piston 28 is moved in the opposite direction, simultaneously pulling back tube 22 and bringing balloon 24 to the configuration shown in FIG. 2(a). As can be seen the arrangement shown eliminates the possibility of the balloon remaining inflated due to defect or accident.

The stem of the catheter (i.e. that part whose function is to be inserted into a patient's body) may be constructed in one piece from a suitable thermoplastics material, preferably one which is radio-opaque, by a suitable combination of vacuum-forming, blow-moulding, injection-moulding and extrusion techniques. Thus, referring to FIG. 3(a), a tube 22 of smaller diameter and a tube 23 of larger diameter may be extruded, with the two tubes being joined by a balloon 24 of appropriate size and shape formed as one part of the overall extrusion process. Then, the simple topological transformation of inverting the tube 22 inside the tube 23, that is the turning of tube 22 inside out in the direction of arrows C, yields the stem 21 of the inflatable catheter as shown in FIG. 2. That stem 21 may then be attached to a handle arrangement as shown in FIG. 2 to provide a catheter with the advantages detailed below.

If desired the stem 21 may be constructed so that the pair of tube ends remote from the balloon 24 are formed to provide means releasably to connect them to a handle portion. Again the handle may comprise an arrangement similar to that of FIG. 2 except that it will include connection means complementary to those of the stem. In an arrangement of that kind a moulded clip as mentioned above may be used to secure the stem to the handle.

It will, however, be understood that in each of the above embodiments other handle arrangements may be employed which generally provide the necessary relative movement of the tubes and the inflation of the balloon.

A catheter as described above possesses a number of important advantages which may be summarised as follows:

(i) The stem of the catheter is constructed in one piece thereby obviating the need to bond together several components. This leads to a much simpler manufacturing process with a very much reduced scrap rate.

(ii) Since a latex dipping technique can be avoided in constructing the present catheter, it is not significantly material dependent, with a consequent increase in the range of materials that may be employed to construct the catheter. Accordingly, advantage can be taken of materials with behavioural characteristics superior to those of rubber and other latexes to fashion catheters whose performance may thereby be further improved.

(iii) The balloon inflation pressure required when the present catheter body is made from certain thermoplastics materials, e.g. PVC, is very much less than that required to overcome the elasticity of a rubber balloon. This makes for easier inflation and, further more removes the danger of collapse of the inflation lumen wall which can result from over inflating catheters of known design.

(iv) The balloon size is not limited as in some prior art designs, e.g. the Mitchell catheter.

(v) The drainage passages of catheters constructed according to the invention have a larger bore for a given outside diameter of the main catheter body stem than is possible with known catheters. This means that flow through the drainage passage is improved for a given catheter size and the risk of blockage of the drainage passage by bodily debris is reduced. Alternatively, since it is important to use the smallest possible size of catheter in order to avoid unnecessary irritation and pressure, which can result in secondary infection and stricture formation, a smaller catheter can be used to obtain the same flow rate as with a larger catheter of known design. This feature makes the present catheter especially useful as a paediatric catheter.

(vi) The use of suitable thermoplastics materials, such as those described above, to form the catheter stem leads to a device with thinner wall construction than with known designs made of rubber materials. At the same time the walls can be rigid enough to permit suction to be applied (as medical circumstances may warrant) without collapse of the catheter walls. Thus, with the present catheter the need for special so-called "haematuria" catheters to which suction can be applied may be removed.

(vii) The catheter construction eliminates the need for "eyes" in the tip of the drainage passage, as is the case with previous catheters. This further improves the flow of material into the drainage pasasge and reduces the risk of blockage which can occur when "eyes" are present.

(viii) Unlike known catheters, the present catheter can be made with a circular cross section since asymmetry is not introduced by the need for a specially fashioned inflation lumen.

(ix) Since the outer tube diameter is not affected by the presence of the balloon, and since the balloon can be kept withdrawn within the outertube, the catheter can "double" as a so-called Nelaton catheter, i.e. one without a balloon.

(x) During insertion and withdrawal of the main body stem of the catheter into and from the patient's body, the balloon 24 is withdrawn inside tube 22. Accordingly, these operations are made easier and cause less patient discomfort than is the case with known catheters in which the balloons, even when deflated, results in a region of greater outside diameter than that of the bulk of the stem.

(xi) Because the balloon can be withdrawn into tube 22 prior to removal of the catheter, the risk of non-deflation of the balloon is eliminated.

(xii) The design of balloon 24 eliminates the need for the catheter to be fitted with a reinforced tip extending beyond the retaining balloon, as is the case with known devices. This eliminates the need for the catheter to be inserted into the body beyond the position minimally required for medical purposes. Furthermore, this enables improved drainage of bodily fluids to be achieved which may, in some cases, obviate the need for a 3-way (or flushing) catheter.

(xiii) By suitable choice of thermoplastics material the present catheter can be constructed with a highly smooth surface on all parts that come into contact with the body or bodily exudates. This considerably reduces the tendency for secretions to cling to the catheter surface and result in encrustation of that surface. This is a feature of especial importance for long term indwelling catheters.

(xiv) Liquid paraffin may be considered as a lubricant for catheterisation in place of the more expensive materials now used, since the balloon 24 can be made of thermoplastics material not susceptible to dissolution. However, depending on medical considerations aqueous gel lubricants containing local anaesthetic may perhaps be preferred.

While the above description is given in terms of a urinary catheter, and while it will be appreciated that urinary catheters made in accordance with the invention will offer a superior replacement for the Foley catheter (a shorter variant of this catheter suitable for women answers a well known need that has not been widely satisfied to date), it is to be understood that this invention is applicable to catheters in general and the above construction generally may be employed for:

Surgical wound drainage catheters,
Rectal catheters,
Gastro duodenal catheters,
Nasal epitaxis catheters,
Intra-aurol catheters,
Endo oesophageal catheters,
Cerebro spinal catheters,
Cardiac diagnosis catheters,
Urinary catheters,
Endotracheal tubes, and other catheters.

In addition to the above-described construction of catheter which offers a superior replacement for what are known as "2-wa" or "simple drainage" catheters, a "3-way" catheter which conventionally includes a third passage to permit the ingress of an appropriate fluid into the body cavity for the purpose of scouring bodily debris from the walls of the cavity and of assisting transport of the debris into and through the drainage passage of the catheter and hence out of the body, can be provided by including a third concentric tube located inside the tube 22. By a suitable complementary modification of the handle portion a third channel into the body may be provided for the purpose of flushing to scour debris.

Alternatively, and preferably, the tube 22 is extruded in such a manner that, as shown in FIG. 4, one or more cylindrical passages 41 are provided within the walls of tube 22. The passages 41 run from end 31 of tube 22 and communicate with passage 36 at a position adjacent the transition of tube 22 into the balloon 24. Passages 41 thus disposed offer a means of passing flushing fluid into the body using a suitable attachment at end 31 while the passage 36 remains as an unobstructed drainage passage.

For some surgical purposes it is in fact desirable to use a catheter which has a tip of some special shape which extends out beyond the retaining balloon portion of the catheter. Thus, for example, catheters with a specially shaped tip include those having:

a standard tip with opposed eyes,
a staggered eye tip,
a whistle tip,
a Tiemann tip,
a Coudé tip,
and others.

By a simple modification of the process of the invention a catheter stem may be formed with a tip of any desired shape without substantially altering the basic stem construction. Thus, referring to Figures 5(a) and 5(b), these illustrate a catheter in accordance with the invention having a tip 42 including opposed drainage eyes 43. As shown the tip is formed beyond the balloon portion which as before may be exposed (FIGS. 5(a) or retracted (FIG. 5(b)).

In the case where in line extrusion is used to form the stem, the larger diameter tube 23 is extruded first, with the tip and the balloon being blow-moulded or vacuum-formed respectively inside and outside tube 23, after which the smaller diameter tube 22 is extruded. Thereafter, tube 23 is inverted over tube 22 since the alternative operation (tube 22 inverted into tube 23) is no longer possible.

In the case where a concentric tube extrusion technique is used, then the process is altered only in respect of the blow-moulding or injection-moulding step, a blow-mould or injection-mould of more complex design being required to form both the balloon and the tip. Alternatively, the inner tube may be preformed, in which case the formation of a joint between the molten polymer from which the balloon is to be formed and the outer surface of the preformed tube is effected at a suitable distance from the relevant end of the tube to provide the necessary tip of preformed tube. In any of these cases the eyes may be formed as part of the moulding operation or separately, e.g. by cutting.

The catheter described with reference to FIG. 2 also can be effectively used for the safe removal of certain foreign bodies from body cavities. For example, removal of stones from the urinary track may be carried out by the technique illustrated in FIGS. 6(a) to 6(b). That technique is as follows:

1. The catheter is inserted into the urethra to bring its tip just below the suspected position of a stone 45 (FIG. 6(a)).

2. Tube 22 is advanced within tube 23 with inflation of balloon 24 as in a "normal" method of operation (FIG. 6(b)).

3. The stone 45 is maneuvered into position so that it drops into the balloon 24 (FIG. 6(c)).

4. Tube 22 is withdrawn through tube 23 with deflation of balloon 24, which leads to the capture of the stone 45 within a protective sheath provided by the catheter (FIG. 6(d)).

5. The catheter together with the now encapsulated stone can be safely withdrawn from the urethra, and such withdrawal may be accomplished if desired by pulling tube 22 etc. through tube 23.

The above procedure can be regarded as a safe and minimally invasive technique unlike most present techniques for achieving this end. Furthermore, it can be adapted for use with the other catheter types we have listed above.

It will be understood, of course, that the invention is not limited to what is described specifically above. For example, by further simple adaptations the above methods can be used to construct a so-called Portsmouth catheter, that is to say a female double balloon urethral catheter which has two fixed balloons 24 and 46 each with its own inflation lumen. Alternatively, the device may be a variant of a Portsmouth catheter, namely a so-called Folastat catheter in which one balloon can be moved along the stem to allow for variations in length of the urethra.

Additionally, the catheter may be a Suprapubic catheter, which is a urinary catheter designed for use in patients whose bladder is easily palpable, i.e. in the case of chronic or acute retention of urine. Such a catheter is inserted into the bladder through, and by puncturing, the anterior abdominal wall and contains a trocar needle fitted within the central passage which acts as a guide to catheter insertion, after which it can be withdrawn. This instrument leads to a significantly lower post-catheterisation infection rate than urethral catheterisation and is preferred by patients to urethral catheterisation.

Still further the catheter may be a microsurgical catheter. Thus, the central lumen of our catheter may contain an assembly of instrumental devices for surgical purposes, e.g. fibre optics for visualization of the body interior, steerable tips, microsurgical tools, etc. For example, the catheter may be a cystoscopic catheter capable of urethra visualization and transurethral resection of the prostate.

We claim:

1. A self-supporting catheter device for passage into a body cavity through a natural or surgical opening in the body, said device comprising:
    a one-piece stem section having primary and secondary ends, being formed from one continuous flexible member comprising:
    concentric inner and outer tube portions having respective first and second ends, said inner tube portion having an interior passage and having an external diameter that is smaller than the internal diameter of said outer tube portion, thereby providing an annular passage between said inner tube portion and said outer tube portion and permitting the relative movement thereof,
    wherein said respective tube portions are each of a length permitting passage of said device into a body cavity, and
    an inflatable end wall portion closing the space formed between said respective first ends of said inner tube portion and said outer tube portion, and covering said annular passage at said primary end, said inflatable end wall portion permitting axial movement of said inner tube portion relative to said outer tube portion,
    whereby axial movement of said inner tube portion relative to said outer tube portion in the direction of said secondary stem end draws said inflatable end wall portion to within said outer tube portion, and movement of said inner tube portion relative to said outer tube portion in the direction of said primary stem end pushes said inflatable end wall portion outside of said outer tube portion, and whereby said inflatable end wall portion can be inflated to a larger dimension, within the body cavity, by supply of a fluid to said annular passage, while maintaining access to the body via said primary passage.

2. A device according to claim 1, further comprising means whereby said inflatable end wall portion is inflated or deflated by respectively advancing said inner tube portion towards said first end of said outer tube portion or retracting said inner tube portion away from said first end of said outer tube portion.

3. A device according to claim 1, wherein said stem section is made from a radioopaque elastomeric material.

4. A device according to claim 3, wherein the radioopaque material comprises a polyvinyl chloride, a poly (ether block amide) or a silicone.

5. A device according to claim 1 further comprising supply means remote from said inflatable end wall portion to permit the supply of a fluid under pressure to said annular passage formed between said inner tube portion and said outer tube portion.

6. A device according to claim 5, comprising connection means for connecting said secondary stem end to a syringe.

7. A device according to claim 1 further comprising supply means remote from said inflatable end wall portion to supply a fluid under pressure to said annular passage formed between said inner tube portion and said outer tube portion.

8. A device according to claim 7, wherein said supply means comprises a piston connected to said second end of said inner tube portion and disposed in fluid tight engagement within a cylinder associated with said second end of said outer tube portion.

9. A device according to claim 7, wherein said supply means is releasably connected to said inner tube portion and said outer tube portion.

10. A device according to claim 1 wherein a third tube having a first end and a second end is disposed within said inner tube portion whereby a flushing liquid may be supplied through said first end of said third tube.

11. A device according to claim 1, wherein said inner tube portion comprises at least one channel formed in the inner tube portion wall and having an opening at each end of said inner tube portion whereby flushing liquid may be supplied through the opening of said channel which is adjacent said inflatable end wall portion.

12. A device according to claim 1 further comprising a second inflatable end wall formed in said outer tube portion whereby said inflatable end wall portion and said second inflatable end wall can be inflated in-line along said stem section.

13. A device according to claim 1, wherein the first end of said inner tube portion includes a tip portion extending beyond in the direction of said primary end, said inflatable end wall portion.

14. A method for forming a device adapted for passage into a body cavity through a natural or surgical opening in the body, the device having a primary end and a secondary end, which process comprises the steps of:
  (i) setting an annular die to a first diameter and extruding an elastomeric material through said annular die to form a first tube portion of a first diameter having a first end;
  (ii) vacuum-forming or blow-moulding the first end of said first tube portion adjacent the annular die to form an inflatable end wall portion;
  (iii) setting the die to a second diameter;
  (iv) extruding the elastomeric material through the annular die to form a second tube portion of a second diameter having a first end and a second end, said first end being joined to said inflatable end wall portion; and
  (v) thereafter inserting the smaller diameter tube portion into the larger diameter tube portion or the larger diameter tube portion over the smaller diameter tube portion to form an annular passage therebetween, and so that the respective second ends of said respective tube portions are substantially equidistant in length from said inflatable end wall portion,
  wherein said tube portions are extruded to a length permitting passage of said device into a body cavity.

15. A method according to claim 14, wherein said passing step comprises the step of passing said first tube portion having a smaller diameter than said second tube portion, into said second tube portion.

16. A method according to claim 14, wherein said passing step comprises the step of passing said second tube portion having a smaller diameter than said first tube portion, into said first tube portion, and
  said vacuum-forming or blow-moulding step further comprises the step of forming a tip portion on said second tube portion which extends beyond in the direction of the primary end, said inflatable end wall portion in the finished device.

17. A method for forming a device adapted for passage into a body cavity through a natural or surgical opening in the body, the device having a primary end and a secondary end, which process comprises the steps of:
  (a) ejecting molten elastomeric material from an annular die for extruding concentric inner and outer tube portions, said tube portions each having a first end;
  (b) moulding, e.g. blow-moulding or injection-moulding an inflatable end wall portion between the tube portions first ends from the molten material; and
  (c) extruding the remainder of the two concentric tube portions to a length permitting passage of said device into a body cavity.

18. A method according to claim 17, wherein the moulding step (b) includes the step of forming a tip portion on said inner tube portion, said tip portion extending beyond in the directin of the primary end, said inflatable end wall portion.

19. A process according to claim 17, wherein said ejecting step comprises the step of ejecting an elastomeric material comprising a polyvinyl chloride, a poly, or a silicone.

20. A process according to claim 17, further comprising the step of treating said device to sterilize said device.

21. A method for forming a device adapted for passage into a body cavity through a natural or surgical opening in the body, said device having a primary end and a secondary end, which process comprises the steps of:
  providing a performed tube portion of elastomeric material having a first and second end and a first diameter;
  disposing said preformed tube portion in an essentially concentric relationship with an annular die for extruding a die-formed tube portion of elastomeric material having a second diameter and a first and second end;
  ejecting at least sufficient molten elastomeric material from the annular die to form an inflatable end wall portion;
  moulding, e.g. blow-moulding or injection-moulding, an inflatable end wall portion between the end of said elastomeric material in the annular die and the first end of said preformed tube portion; and
  extruding a die-formed tube portion while passing said preformed tube portion in the same direction as the extrusion, and at the rate of the extrusion,
  wherein said preformed tube portion is of such a length, and said die-formed tube is extruded to a length, permitting passage of said device into a body cavity.

22. A method according to claim 21, wherein said extruding step comprises the step of extruding a die-formed tube portion having a larger diameter than said preformed tube portion.

23. A method according to claim claim 22, wherein said disposing step comprises the step of disposing said preformed tube portion in a manner whereby a tip portion of said preformed tube portion extends beyond in the direction of said primary end, the position at which said inflatable end wall portion is moulded.

24. A method according to claim 14, wherein the step (i) comprises the step of extruding an elastomeric material comprising a polyvinyl chloride, a poly, or a silicone, and
  said step (iv) comprises the step of extruding an elastomeric material comprising polyvinyl chloride, a poly, or a silicone.

25. A method according to claim 14, further comprising the step of treating said device to sterilize said device.

* * * * *